United States Patent
Eigen et al.

(12) 
(10) Patent No.: US 6,423,516 B1
(45) Date of Patent: *Jul. 23, 2002

(54) PROCESS AND AGENT FOR INSTABILIZING VIRAL QUASI-SPECIES-DISTRIBUTIONS AVOIDING RESISTANCE PHENOMENA

(75) Inventors: Manfred Eigen; Andreas Schwienhorst, both of Göttingen; Christof Biebricher, Adellebsen; Björn Lindemann, Göttingen, all of (DE); Esteban Domingo, Colmenar Viejo (ES); John Holland, Solana Beach, CA (US); Karsten Henco, Erkrath (DE)

(73) Assignee: Evotec BioSystems AG, Hamburg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 50 days.

(21) Appl. No.: 08/362,604
(22) PCT Filed: Feb. 7, 1993
(86) PCT No.: PCT/EP93/01711
§ 371 (c)(1), (2), (4) Date: Mar. 22, 1996
(87) PCT Pub. No.: WO94/01545
PCT Pub. Date: Jan. 20, 1994

(30) Foreign Application Priority Data

Jul. 7, 1992 (DE) .......................................... 42 22 289

(51) Int. Cl.[7] ............................. C12P 19/34; C12P 7/34; C12Q 1/68; C07H 21/04; C07H 21/02

(52) U.S. Cl. .................. 435/91.2; 435/6; 435/91.33; 435/172.1; 435/172.3; 435/152.3; 435/235.1; 436/94; 536/23.1; 536/23.5; 536/23.72

(58) Field of Search ...................... 435/6, 91.1, 91.2, 435/91.33, 235.1, 172.1, 172.3, 252.3; 436/94; 536/23.1, 23.5, 23.72

(56) References Cited

PUBLICATIONS

Konarska et al Cell 57:432–431 1989.*

* cited by examiner

Primary Examiner—Eggerton A. Campbell
(74) Attorney, Agent, or Firm—Collard & Roe, P.C.

(57) ABSTRACT

A process for instabilizing viral quasi-species-distributions under avoidance of resistance phenomena by replication of the nucleic acids of the viruses present in the quasi-species-distribution by of a defective replication system, a) whereby the defective replication system has a rate of misincorporation for nucleotides above the rate of misincorporation of the viral wild-type-replication system and, whereby the viruses are replicated by the replication system having the higher rate of misincorporation at least as effectively as it is done by the replication system of the wild-type virus, b) and/or negative influence of the replication of the consensus-sequence (nucleic acid sequence of the wild-type virus) in relation to other replicatable nucleic acids.

14 Claims, 8 Drawing Sheets

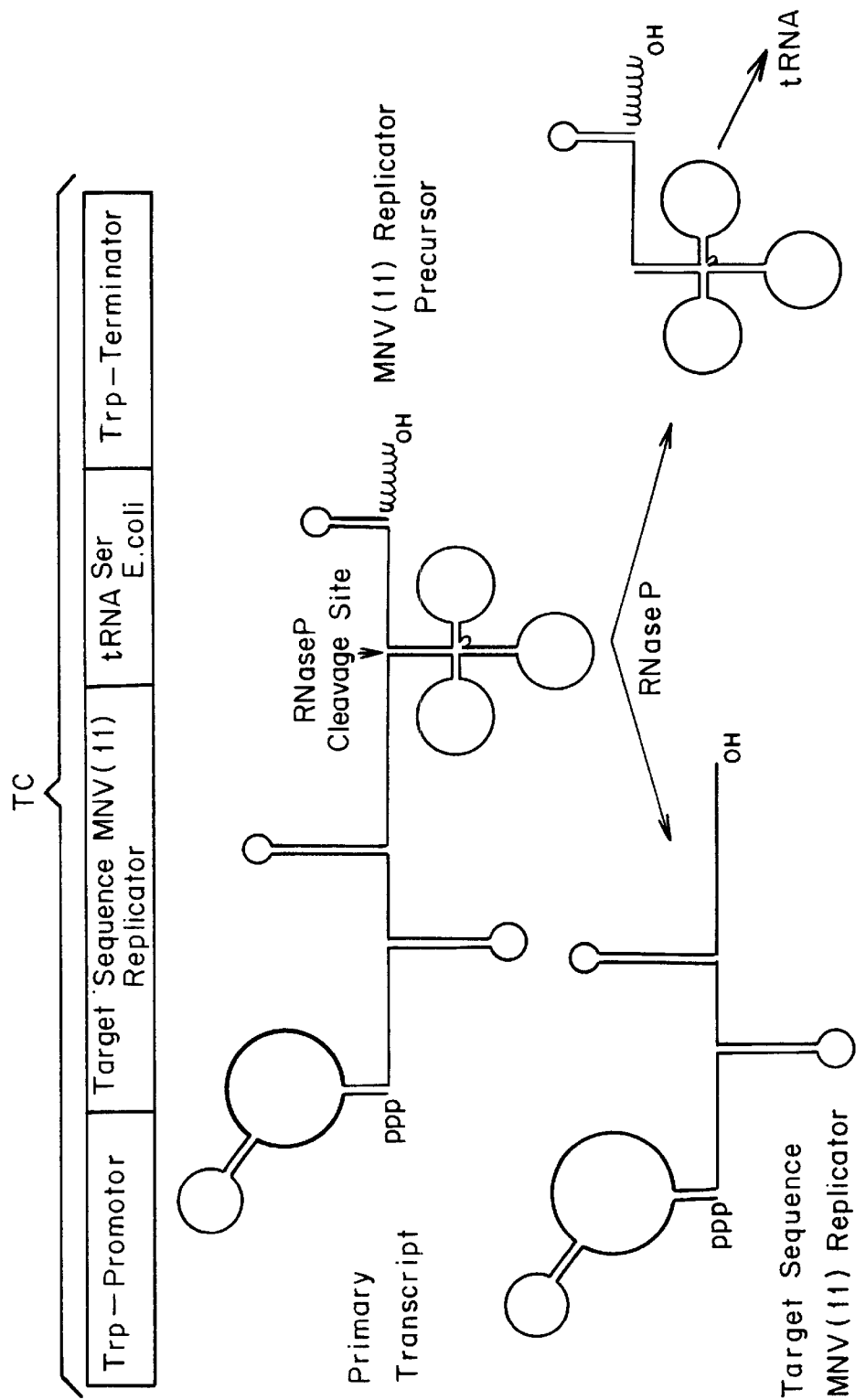

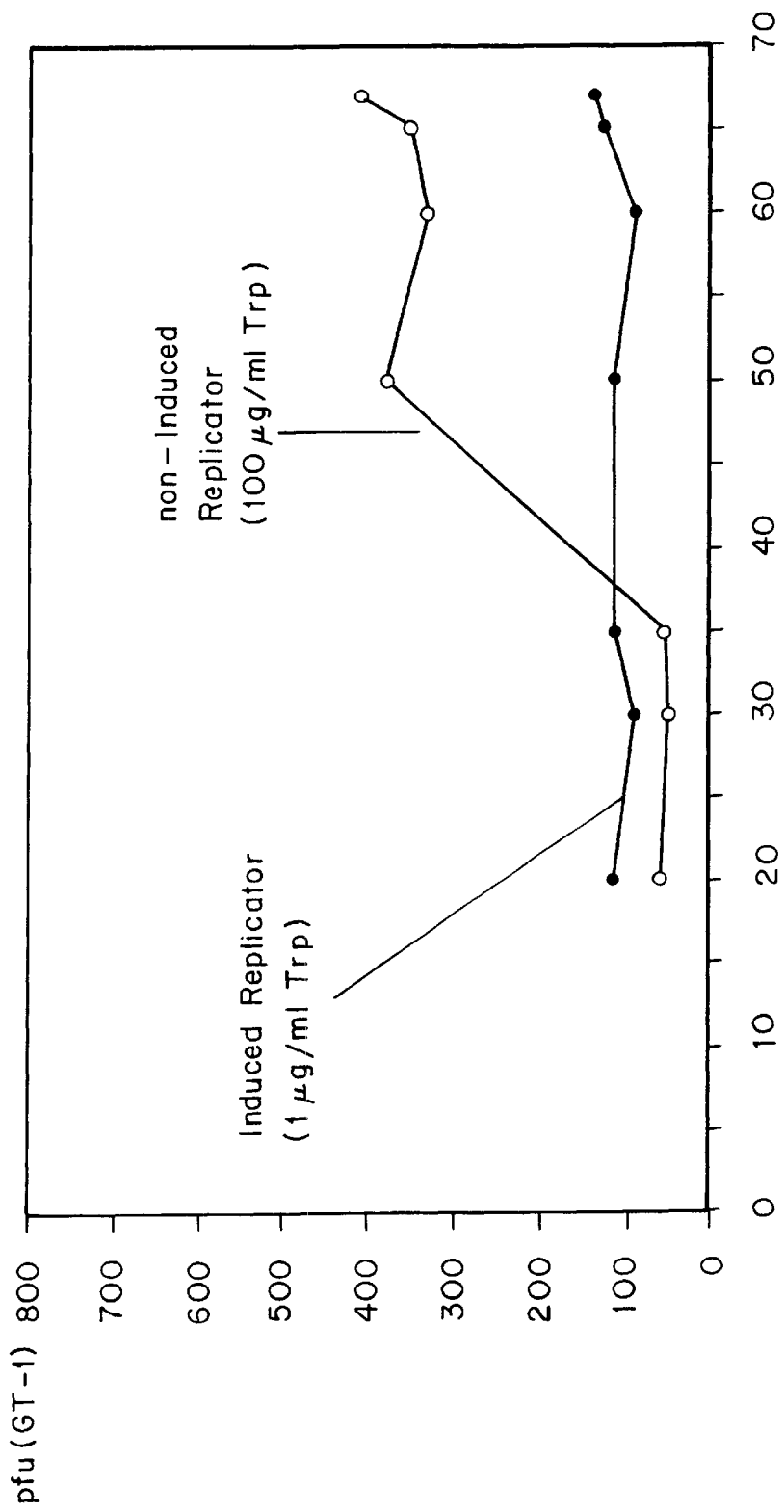

Figure 1:
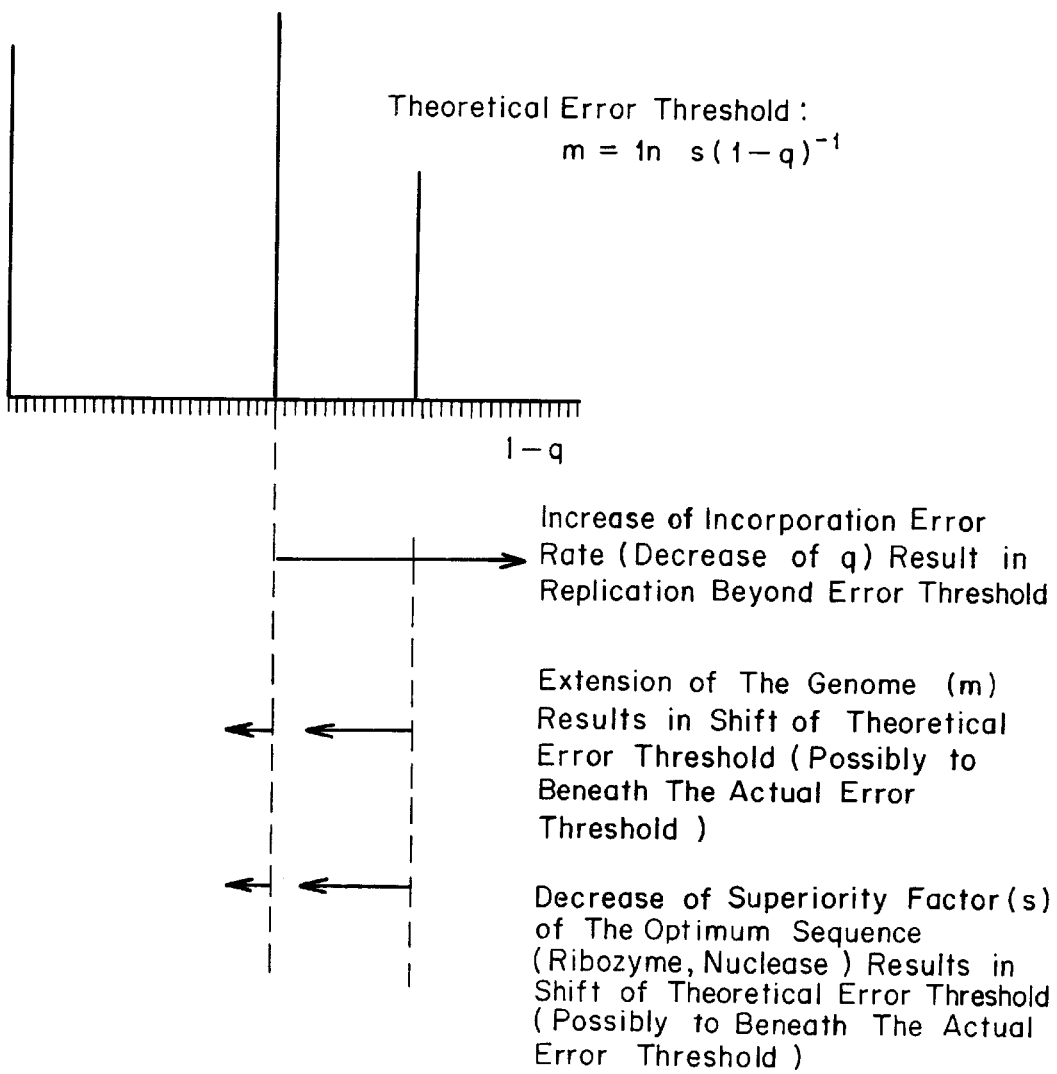

FIG. 5
QUASI SEPCIES DISTRIBUTION WITH PROCEEDING
REPLICATION TIME t1, t2, t3,
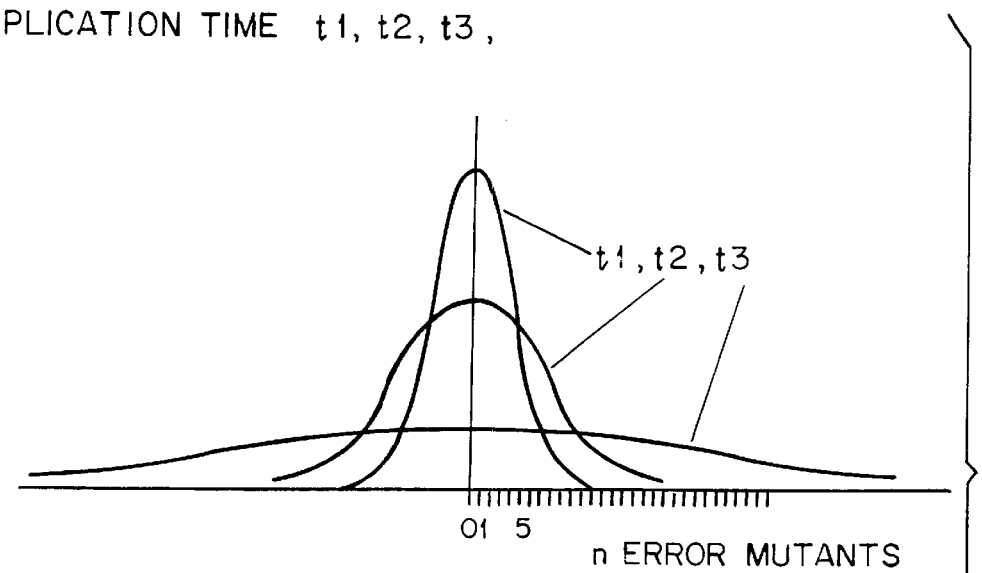
ANALYSIS OF QUASI SPECIES DISTRIBUTION
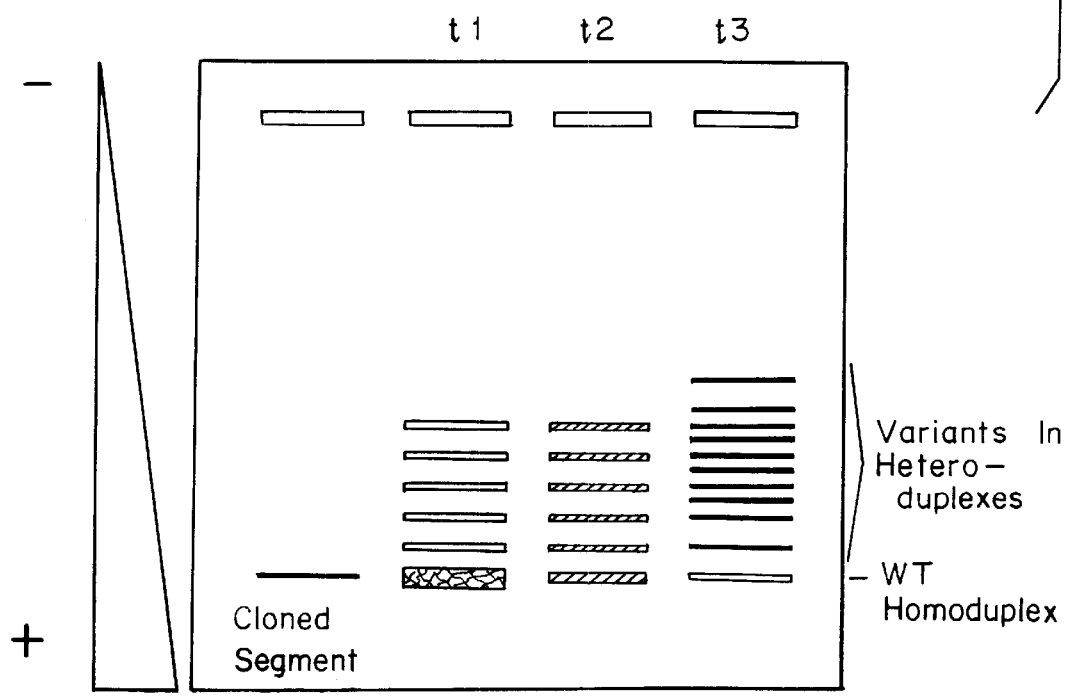

ANALYSIS OF CLONED POLYMERASE GENES BY QUANTITATIVE DETERMINATION OF THE MUTATED SYNTHESIS PRODUCTS

PROCESS AND AGENT FOR INSTABILIZING VIRAL QUASI-SPECIES-DISTRIBUTIONS AVOIDING RESISTANCE PHENOMENA

This application is a U.S. national phase filing under 35 U.S.C. §371 of PCT/EP93/01711, Feb. 7, 1993, and claims priority from Federal Republic of Germany application P 42 22 289.3, Jul. 7, 1992.

The invention relates to process for instabilizing viral quasi-species-distributions avoiding resistance phenomena by replication of the nucleic acids of the viruses present in the quasi-species-distribution by an defective replication system. Subject matter of the present invention is also an agent for executing the process according to the invention as well as nucleic acid sequences obtainable by reaction of viral replication systems with nucleotides.

Illnesses caused by viruses have been found in the hitherto existing pharmacology to be extremely difficult for treating by therapy. Up to now used conventional antiviral treatment strategies are exclusively concentrated to substances and methods having the aim to specifically suppress the reproduction of a virus in order to stop the infection in this way. This can be attained by different action mechanisms. A suitable point of attack of the reproduction of the virus is the specific virus replication system or one of the components thereof. In such a way, the viral replication apparatus can be inhibited by antimetabolites as AZT (HIV, AIDS) or Acyclovir (HSV, herpes). Other strategies are related to virus-coded enzymes which are assuming functions in quite specific replication phases of the virus. For instance, the viral protease for cleavage of polypeptide-translation products or also active principles which, e.g., prevent the built-up of a virus or prevent the release of the virus genom in the cell after infections, are belonging to The mentioned strategies have in common that they will cause after a relatively short period of time resistance phenomena, such that the treated viruses avoid a drug therapy. In this case, the period of time, until the resistance phenomena will occur, can vary strongly for different active principles and viruses and can last for days up to years.

M. Eigen has been successful, to explain the property of the rapid adaptability of the quasi-species-distribution [M.Eigen (1971), Naturwissenschaften 58, 465–523]. By a quasi-species is understood that the "wild-type"-genome does not consist of a defined sequence which have all viruses of one species, but of a stable distribution of sequences of which the most frequent specific sequence is corresponding to the wild-type. It is identical with the consensus sequence which is obtainable if at every position or sequence the most frequently occurring nucleotide, respectively, is used [D. A. Steinhauer and J. J. Holland (1987), Ann. Rev. Microbiol. 41, 409–433]. However, the majority of the sequences is not identical with the wild-type sequence. That means, that indeed the viral genome is macroscopically defined and determinable as consensus sequence, but it is microscopically present in the form of a mixture of many mutants which are permanently in competition with one another. This competition maintains the genetic information of the virus in a dynamic equilibrium of mutation and selection. The genetic information modified by mutation is always re-established by selection, in such a way that the infection chain is maintained [Domingo, E., Sabo, D., Taniguchi, T. and Weissmann, L. (1978), Cell 13, 735–744].

By using a quasi-species-distribution, a population of microorganisms can adapt extremely rapidly to different environmental conditions. If, for instance, the temperature conditions change in the environment of a virus population, it is possible that the existing wild-type is in no way the variant which is reproducing most successfully under the new circumstances. Another variant among the great spectrum of the quasi-species-distribution is perhaps more suitable to replicate under the changed temperature. Possibly, also only some additional mutants are needed for a better adapted variant starting from a variant of the quasi-species-distribution instead of a wild-type sequence. By this mechanism, the great flexibility will become understandable, by which the microorganisms can adapt to changed environmental conditions in a surprisingly short period of time.

This flexibility can be paid by a high portion of lethal or partially defect descendants in the virus population. As a matter of fact, only a fractional part of the released viruses is infective in normal virus populations. The viral population can not stand to an increase of the rate of misincorporation of the viral replication system, e.g., in the case when the rate of misincorporation surpasses the theoretical error threshold belonging to the replication system. The portion of defect descendants will become that high that the infection chain can no more be maintained for a long time by viruses which still are infective.

For two reasons, this strategy is specifically directed against the distribution of viruses, especially of RNA-viruses. The viruses contain in most cases—contrary to their hosts—RNA as a genetic material. In order to enable a reproduction of the viruses, the virus must code itself at least the most important parts of the replication apparatus, since it can not fall back on the constituents of the host. Due to the lack of complicated error correcting mechanisms, narrow limits are set to the replication accuracy by the physical/chemical nature or the base-pair. The rates of misincorporation are realized in the range of between $10^{-3}$ to $10^{-5}$ with RNA-viruses. Furthermore, the selection is limited with viral genomes. Host cells divide after doubling their genomes and defect chromosomes become immediately apparent by disadvantages to the cell, as far as functionally needed gene places are concerned. Therefore, virus genomes are accumulated in infected cells to great populations. Defect gene products on single genomes do not cause disadvantages to the defect genome itself, because all genomes are participating in the same way to the common production. There is also no prejudice for defect matrices within the replication, such that the propagation of error is practically not hindered in the beginning. Only with some few viruses, the infective strands are read out in the late infection phase to a matrix (master template) in the meaning of a rolling-circle-model and, therefore, the propagation of error is controlled. Defects in the genome of a virus become only apparent during the next infection and only then can be eliminated by selection.

Theoretical calculations support the findings that a distribution of quasi-species-information can be maintained only in a stable way during facultative periods of time as long as a certain error threshold of the replication apparatus is not exceeded. Computer simulations have been found to give definite correlations between a pattern of selection advantages, a rate of replication error and the stability of the quasi-species-distribution. The calculation predicts a diffluence of information and therefore, the termination of a quasi-species-distribution in the vicinity of the wild-type sequence, if this error threshold is exceeded.

The relationships described by Eigen clarifies the dilemma in which the classical search for active agents is involved by screening of the active materials. When antiviral materials are discovered which prevent the propagation of the virus population by reproduction (replication), a "selection pressure" is exerted to the viral quasi-species-distribution, in such a way, that resistant mutants are formed which are the basis for a new viral quasi-species-distribution. Certainly, some of this quasi-species will be infective again, such that the viral infection is maintained by a new quasi-species-distribution. Therefore, the common conceptions of today for the so called "drug-screening" are even dangerous because of the permanent danger that new, possibly even stronger pathogenic viruses, are induced by this undesired selection pressure.

The object of the present invention is to provide a generally applicable process by which the virus population lose certain pathogenic properties, particularly the property of infectiousness. Related to this is the provision of an agent by which viral infections can be treated therapeutically and prophylactically without stimulating the formation of resistent virus populations.

The nucleic acids described are particularly useful to effect in the process according to the invention the instabilization of quasi-species-distributions by diminution of a superiority parameter (s).

An agent is particularly suitable for carrying out the process according to the invention.

The theoretically deduced relation of the error threshold (see below) constitutes the parameter s superiority parameter (superiority) and (1-q) (rate of misincorportion). These parameters constitute the basis of the process according to the invention for exceeding the maximum permissible rate of error, the theoretical error threshold. In this way, the quasi-species-distribution is becoming unstable.

The process according to the invention exploits the instabilisation of a viral quasi-species-distribution which is based upon the replication of this distribution with an incorrect replication system. Thereby, the incorrect replication system has a rate of misincorporation exceeding the rate of misincorporation of the wild-type replication system. The rate of misincorporation is a measure of accuracy by which a given viral replication system of a quasi-species-distribution can replicate a genome.

The rate of misincorporation of the polymerase from HIV-1 is, for instance, $1 \times 10^{-4}$. This means that no more than in the range of about 10 kb-genomes can be amplified in a stable way. This relates to about the length of the natural virus-genome.

To begin with, Eigen et al. (1971) deduce from pure theoretical considerations the error threshold of a replicative system. A relation between the quantities q, m, is established:

$$m = \ln s(1-q)^{-1}$$

s: A superiority factor (s) of the replication efficiency in relation to the replication efficiency of the totality of all potential mutants is roughly simplified assigned to the specific sequence of the highest concentration (consensus-sequence, former "wild-type" definition) in biological systems.

m: The length of the to be replicated sequence in nucleotides or base-pairs.

q: The relative, average rate for the correct incorporation of the complementary Watson-Crick nucleotides in relation to the individual position. (1-q) relates to the error threshold.

In the case of an approximate formula, it clearly describes that a replicative system having real characteristic numbers q, m and s can only replicate below a certain error threshold without diffluence of the information.

Previous antiviral strategies try to suppress the replication per se. The hereby presented process is based on knowledge derived from the relation of the error threshold. Three parameters are resulting from the relation of the error threshold which can be used according to the invention in order to induce a replication beyond the natural error threshold. A central parameter is, as will be seen later on, the parameter q which can be diminished to lower values by measures according to the invention without influencing the efficiency of the replication as a whole.

The parameter m is useful, when the length of the sequence to be replicated would be elevated by artificial prorogation of the genome while maintaining the other characteristic data. This happens sometimes by ignorance of the consequence and unwantedly, when, e.g., during the preparation of recombinant products, their coding sequence is incorporated into filamentary phages and, an instability of the phage is observed. In this case, evidently, the relation of the error replication system is violated.

When $m = \ln s(1-q)^{-1}$, then the actual rate of misincorporation of the natural system is equal to the theoretical error threshold of this system. Now, when exceeding this theoretical error threshold, then mutants of the quasi-species-distribution are formed in a progressive way, a fact that is finally leading to an enlargement of the quasi-species-distribution.

This relation is outlined in FIG. 5. The FIG. 5 describes schematically the quasi-species-distribution of a wild-type-population of a virus. The abscissa indicates the quantity of sequence variations, x=(0) means the consensus of the virus which is denominated as "wild-type". The appropriate y-value indicates its respective portion of the population. The experiments of Domingo et al. (1978) with the $E.$ $coli$ virus Qβ have shown that the wild-type is only the relatively most abundant, specific sequence. However, the majority of the bacteriophages represent the 1-, 2- and more-error-mutants of this sequence, which as a whole forms a distribution which yields the wild-type sequence. The width of the distribution remains normally stable while maintaining the growth conditions. However, the mutant spectrum is enlarged when the replication is subject to greater errors. When the replication is beyond the allowed error threshold, the quasi-species-distribution attains no new equilibrium. The distribution will become continuously broader with progressive replication (t1, t2, t3), until finally the information flows off completely. It comes to the "error catastrophy". The virus is extincted.

An important criterion of the process according to the invention is the demand that the replication of the quasi-species-distribution, which has the replication system with higher error misincorporation than the natural distribution, proceeds at least as efficiently as the replication of the quasi-species-distribution of the viral wild-type.

A second central prerequisite of the process according to the invention is that the polymerase or polymerase subunit replicates specifically the correspondent viruses for the respective virus beyond the error threshold, without being less efficient in this case than the correspondent wild-type component. Efficiency means in this case the rate of synthesis of the genomes of the new virions. Therefore, it is necessary that the rate constants for the processes of initiation, elongation and the termination do not differ considerably from the respective constants of the wild-type units, such that altogether, the mentioned condition is at least accomplished. Preferably, this even means a considerably accelerated process which may be established when, e.g., proof readings are claimed to a less degree or are not claimed at all.

The process according to the invention is based on the surprising finding that in the meaning of an evolutionary virus distribution, a defective degeneration at a high amplification rate is as unfavorable as the inhibition of the virus replication. According to the invention, further aspects are resulting from the strategy upon which the invention is based, which are related to the tendency to produce resistant variants which can avoid an antiviral therapy.

These undesired phenomena are becoming obvious at the present in the AZT-treatment of HIV-infected patients. Whereas in the beginning, a positive success of the treatment seems to appear and decreasing virus titer can be observed, AZT-resistant virus variants are appearing during a period of some weeks to months. In these cases, a transfer to in vitro cell cultures shows very clearly that an inhibition of the virus replication would necessitate a dosage of the therapeutic agent which is higher in order of magnitudes, in order to merely attain a half-maximum virus replication. This is being out of question on behalf of the systematic treatment of the erythropoietic system with such toxic concentrations of AZT.

The defective replication of the viral nucleic acid can be induced, according to the invention, preferably by action of a chemical substance. In this case, the substance can act as an antimetabolite or allosteric effector of the replication system. The substance is preferably of such a kind that it does not interact with the cellular enzyme system, in order to prevent, optionally, the toxic side-effects. Side-effects of such a kind are appearing almost imperatively, when the interference with the replication as a damming of the replication system is used as a mechanism to inhibit a virus infection. As an example of this kind, the negative effect of AZT to the erythropoietic system during the treatment of HIV-infections should be mentioned.

In a preferred embodiment of the process according to the invention, the defective replication system is a variant of a natural mutant system of the quasi-species-distribution. The defective replication system may also be mutant produced by mutagenesis.

Preferably, the target cells of the virus infection (target cells) are put in a position, by infiltration of a viral replication system into the virus population with subsequent infection of the target cells, to replicate a virus above the replication-error threshold of the viral replication system. That means, that the rate of replication error is higher in this case than that of the respective wild-type quasi-species-distribution. Also, by direct infiltration of a viral replication system or components of a viral replication system into the target cells, the latter can be put in a position, to replicate a virus above the replication error threshold of the viral replication system, i.e., with higher rate of replication error than that of the respective stable quasi-species-distribution. In this case, the condition is always fundamental that the efficiency of the replication of the mutant with the defective replication system is at least as good as that of the respective wild-type quasi-species-distribution.

RNA or DNA polymerases or co-factors of RNA or DNA polymerases are used as preferred replication systems.

Preferably, according to the invention, the infiltration of the defective replication system into the virus population by transformation of individuals of the respective virus population or of the target cell is carried out in a per se known manner. In this case, the known processes of the gene therapy are possible.

However, the infiltration of the defective replication system can also be done by superinfection of the target cell with defective viruses of the same species which carry the defective replication system.

In viruses, the replication above the natural error threshold of the stable quasi-species-distribution, almost always signifies also a replication above the admissible error threshold. In this case, the efficiency of the replication should not be worse than in the case of the quasi-species-distribution of the wild-type, since the correct working polymerases can always be present, too. If this condition is not maintained, and the mutants with defective replication system are not reproduced in such an efficient way, the latter will be such diluted after several replication cycles, that they no more play a role in the quasi-species-distribution.

In the alternative 1b) according to the main claim 1, nucleic acid sequences are preferably used which are available by reaction of nucleotides and a viral replication system as well as other buffer salts and energy resources which are necessary to the reproduction of viruses. In this case, oligo- and polynucleotides are formed from the nucleotides of the viral replication system, which exclusive genetic information only comprises its own maximum amplification. This system, preferably in a cell-free form, optimizes also oligo- or polynucleotides by selection to a maximum amplification of this sequence by mediation of the viral replication system. In this case, under other circumstances. e.g. by using other viral replication systems, respective, different oligo- or polynucleotide sequences are obtained. Also, by action of external influences like temperature or buffer conditions, another oligo- or polynucleotide sequence can be induced.

The usable nucleic acid sequence (replicators and replicator-precursors) according to the invention are preferably nucleic acid sequences which are partly homologous or identical to such substances which are formed in vitro or intracellularly, if by or with cooperation of the viral replication system it is concurrently selectioned to the most rapidly replicating variant, without all or some functions which are necessary to the wild-type virus, particularly, protein-coded functions or the expression regulating functions, being preserved. This practically, that nucleic acid sequences are used which, besides of the information that they can be particularly well reproduced, do not have to have other viral genetic information.

In the past years, different antiviral strategies have been discussed which apply RNA-molecules interacting with viral RNA.

In such a way, e.g., antisense-RNA is known which via hybridization on viral RNA, directly prevents the translation of viral proteins (Coleman et al., 1984, Coleman et al., 1985, Hirashima et al., 1986), or which is exposing them, particularly, in such a way to cytogenous RNase-activity (Agrawal et al., 1988). However, it must be assumed that the intracellular formation of duplex-RNA-structures between antisense areas and sense-RNA, needed for that purpose, under native conditions, is not an efficient process. Furthermore, ribozymes which, via antisense areas, recognize and can cut specific viral RNA-sequences are known (Sarver et al., 1990; Rossi et al., 1990; Weizsacker, 1992). However, such ribozymes can also represent a high systematic burden, due to their toxicity against cellular RNA. Furthermore, since the first experiments made by Spiegelmann with the Qβ-system, molecules in evolution experiments have been optimized to maximum replication ability under different boundary conditions in this system (Mills et al., 1987; Levisohn et al., 1989; Biebricher, 1987; Bauer, 1990). However, small RNA-replicators have also been made known for other viral polymerases (Konarska et al., 1989; Leary et al., 1991).

Viral polymerases can be effectively impeded to replicate the natural substrate (viral genome), if a natural replicator is offered which has at least one of the following properties:

the replicator has intracellularly a significantly shorter replication time than the natural viral substrate;

the binding constant of a replicator to the respective polymerase is greater than that of the natural nucleic acid;

preferably, the replicator has as few as possible, particularly preferred no, binding sites to effectors with negative feedback-effect to the replication as, for instance, ribosomal binding sites or binding sites for inhibiting factors dating from a later phase of the replication like, e.g., coat-proteins.

The strategy according to the invention has the advantage that the not infected host cell expresses the replicator or the replicator-precursor molecule only to a small amount and, provides for a strong amplification only after infection in the presence of the viral replicase. In this way, this strategy causes the active agent to be formed specifically in the infected cell by autocatalysis and presents by this way a quasi ideal form of "drug targeting". Apart form the fact that the systematic toxicity—being estimated as low in any way—of a small nucleid acid being non-functional at low concentrations like RNA or DNA, furthermore, possible side-effects will be limited by this mechanism.

In a preferred embodiment of a transgenic host system, the possibility can also be realized to express the replicator, or preferably its precursor, not at all constitutively, but to control the nucleic acid by a regulation element. Particularly, a promoter or a replication origin which may be activated in trans by viral components after the infection, and which liberates the replicator or its precursor, comes into consideration as such a regulation element.

By using RNA-replicators, of which the precursor molecules being infiltrated as DNA into the host cell, preferably, the cellular post-transcriptional maturation system, as described below in the given example, can be used in order to produce authentic terminals of the replicator-RNA. Apart from that, it is not possible without any difficulty to produce transcription products which correspond to the essential replicase-binding characteristics of the terminals of replicator molecules. The example shown below describes the precursor of a RNA with tRNA-fusion which is processed via the cellular system of the RNase P.

The nucleic acid sequence, usable as a replicator or replicator precursor according to the invention, carries a nucleic acid part from which the replicator is formed intracellularly by of polymerases, whereby the precursor molecule additionally contains portions which enable the transport to a target cell and/or which enable a stable integration of the replicator segment into the genome of the target cell.

The following example describes the production of a replicator precursor and of the replicatQr which prevents the distribution of the Qβ-virus in *E. coli*.

FIG. 1 describes the actual rate of a natural replication system.

FIG. 2 describes the construction of the precursor transcript having replicator property for the inhibition of the Qβ-amplification in *E. coli*. The primary transcript is controlled by a Trp-promoter. The proper functionable target sequence needs a precise 3'-end in order to function as replicator for the Qβ-replicase. This can be achieved by the immediate use of a direct transcripts only in an inadequate manner or not at all. However, the cellular RNase P-system can be used by incorporation of a t-RNA-fusion sequence in such a way that the primary sequence processes into the functional replicator.

Figure 3A:
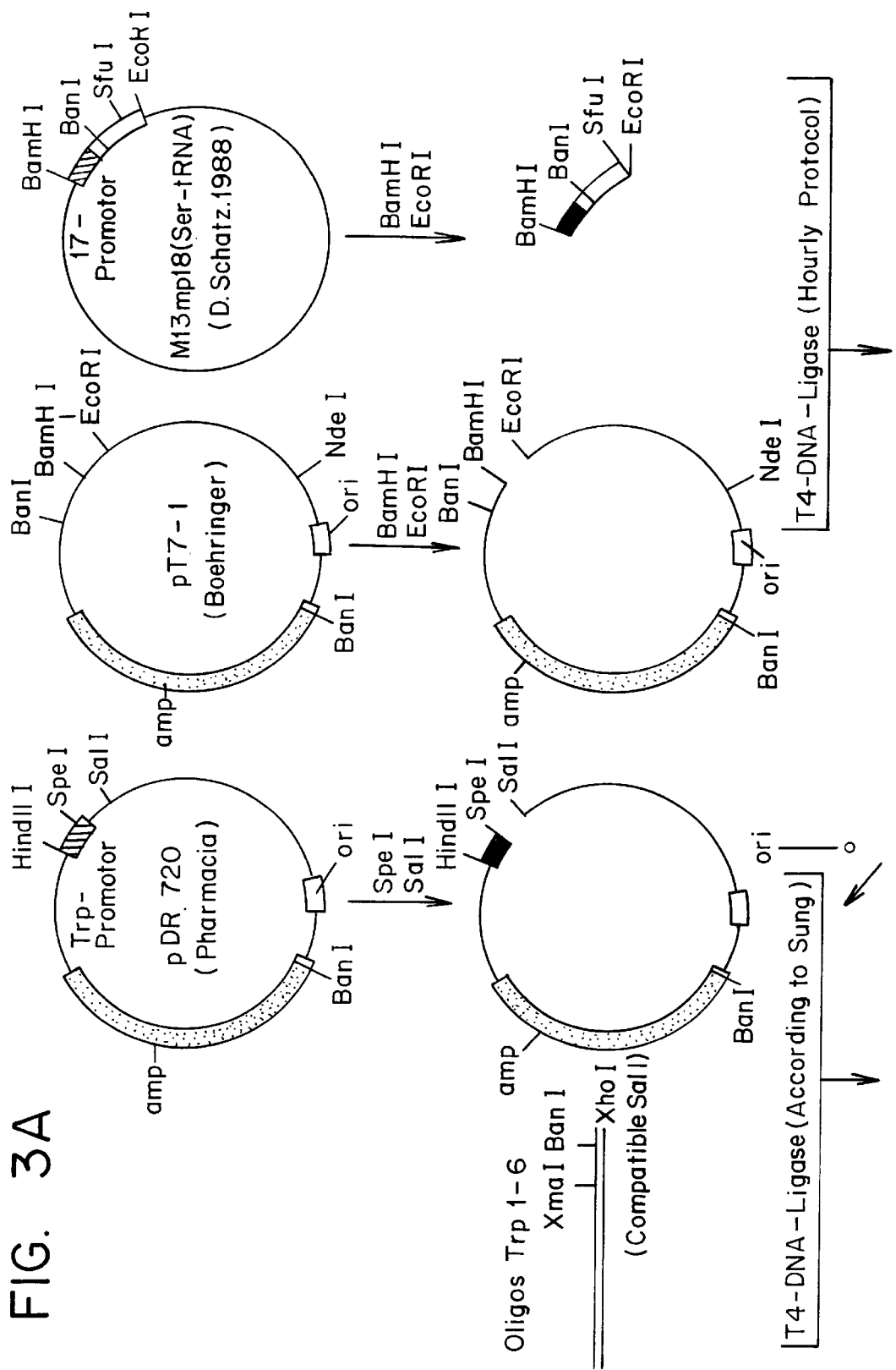
Figure 3B:
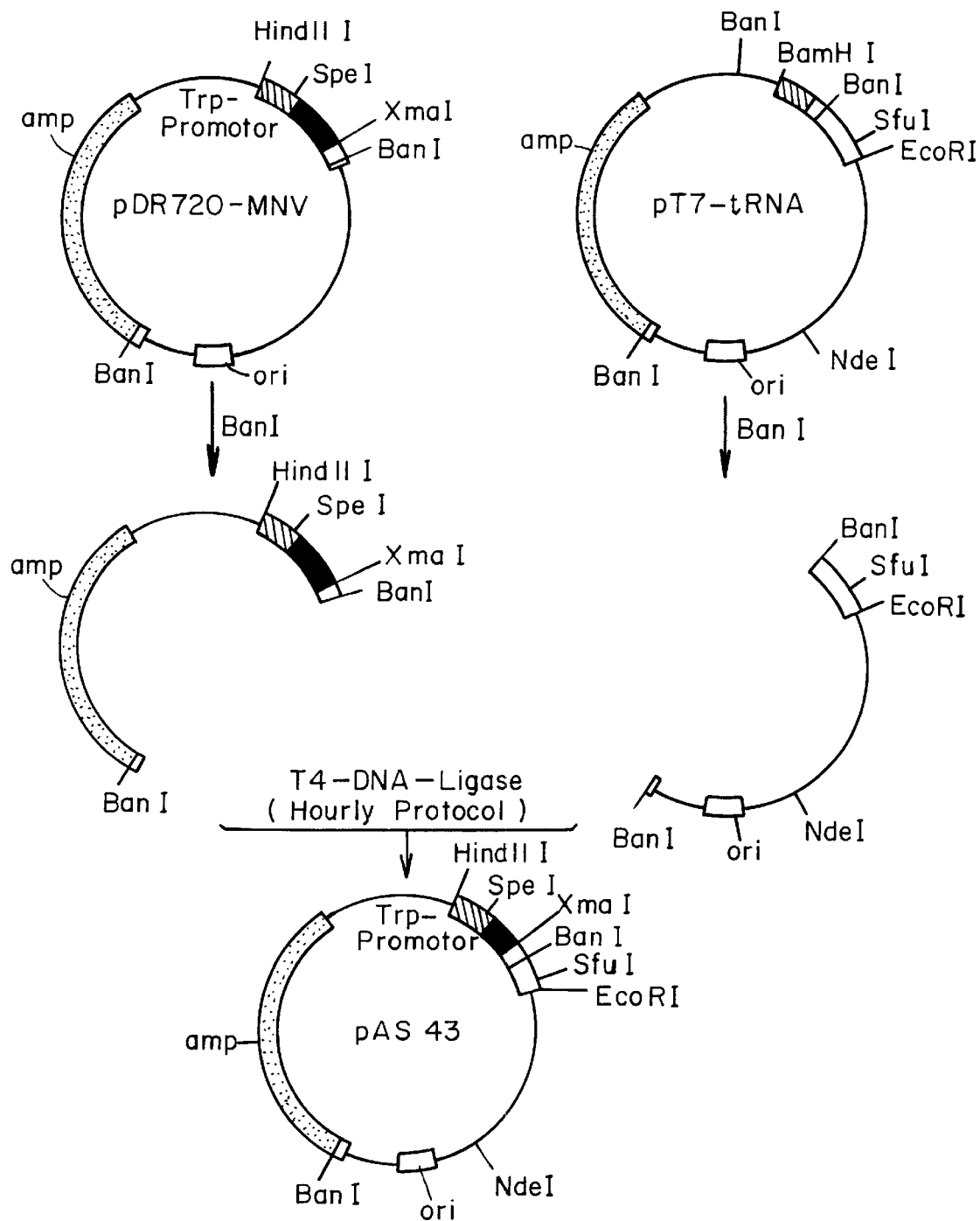
Figure 3C:
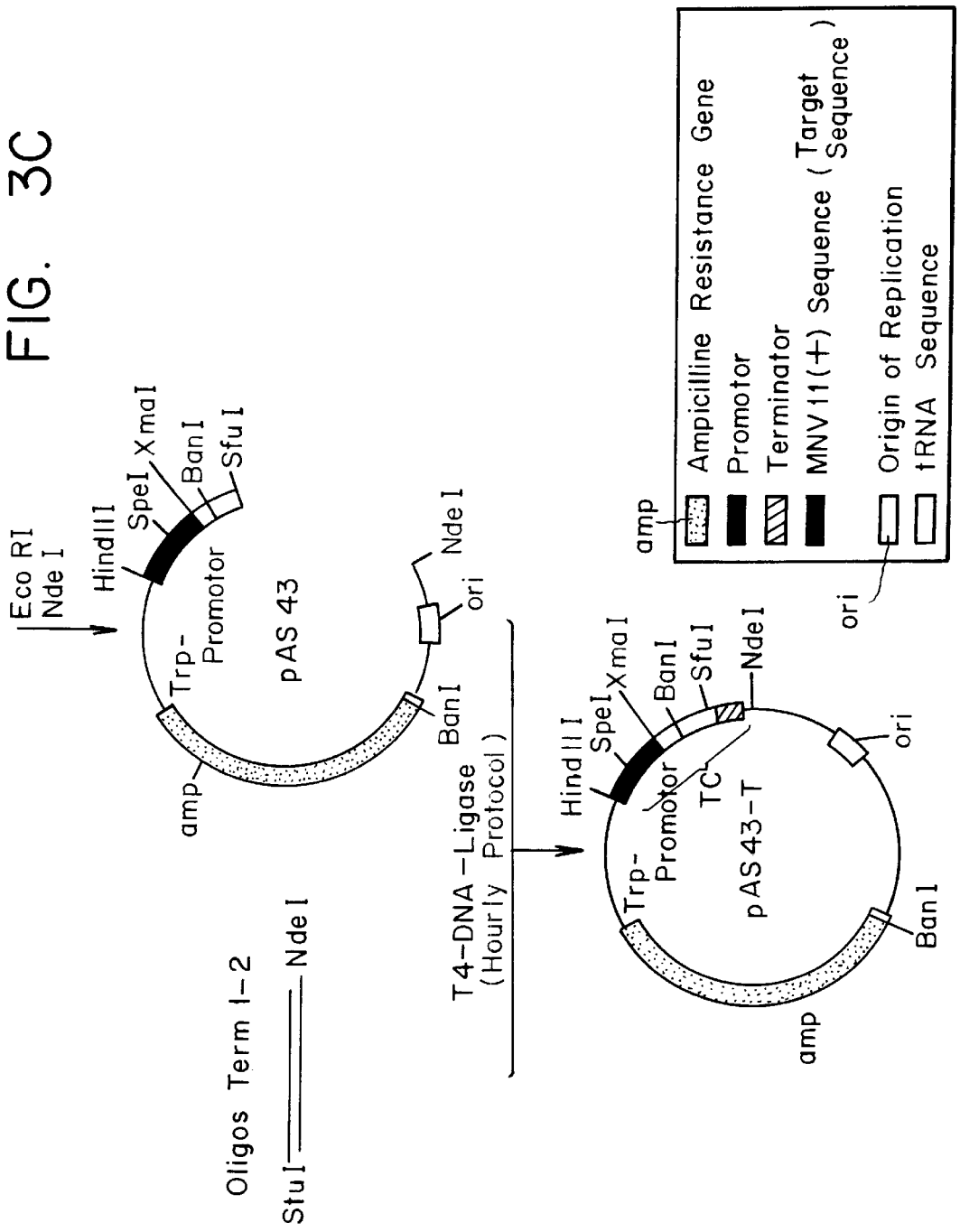

FIG. 3 describes the construction of the structure described in FIG. 2, which was integrated into a plasmid (Pas 43t). The processes applied therein, are per se known processes of the gene technique.

The FIG. 4 shows the blocking effect of the infiltrated nucleic acid sequence to the Qβ-replication. The experiments were carried pout in minimal medium in a Cell-Stat-System. It is evident, that only with switched off Trp-promotor (100 µg/ml) a "burst" of the cells and an initial liberation of Qβ-viruses is achieved after about 50 minutes.

In a preferred variation, the characteristic superiority parameter (s) of the virus replication is diminished by a combination of the replication system and one or more nucleases, ribozymes and/or antisense-RNA. In this case, at least one nuclease and/or ribozyme and/or antisense-RNA is directed towards components of the respective virus-genome. The error threshold, i.e., the still maximally tolerable rate of misincorporation of the respective replication system, is defined as well by the viral genome length as by the superiority of the most successful replicating sequence. However, if the most successful replicating sequence is destroyed by nucleases and/or ribozymes, this consequently will result in a diminution of the characteristic superiority parameter (s).

To sum up it can be said that according to the invention the instabilization of a viral quasi-species by the alternative lb) of the main claim can be attained by coamplifying replicators, i.e. nucleic acid sequences, by of the viral replication system with the viral nucleic acid. Thereby, the efficiency of the replication of the replicators must be higher than that of the viral consensus-sequence, the superiority of which does not exist anymore.

According to the invention, the viral gene for the replication system having the higher rate of misincorporation according to alternative a) of the process according to the invention will be provided with further regulating gene segments, which assume further controlling functions in the transformed virus individual or in the transformed target cell. They can, for instance, take care that the defective expressing system, particularly after the accomplished virus infection, is activated. Preferably suitable are trans-activated regulation sequences which can be used as regulating gene segments, to also provide for a desired, enhanced rate of replication of the virus population.

The target cells of the viral infection, respectively the host cells of the viruses, can be monocellular organisms or bacteria, particularly plant cells or animal host cells as blood cells or erythropoietic stem cells.

The present invention is based upon the findings that the rate of misincorporation of the enzymes which participate in the replication is directly linked to the length of the genome to be replicated. Thereby, the genome is a measure for the complexity of the genetic information and of the replication advantage of the wild-type sequence towards the sequences of the mutant spectrum. An analysis of the misincorporation rates of polymerase of natural organisms and viruses resulted that viruses with great genome length have polymerases with low rate of misincorporation, whereas short-chain genomes with great rate of misincorporation can thoroughly replicated in a reliable manner without flowing off the stored information. The measured in vitro-data are in good agreement to the theoretically predicted data, assuming that a viral system uses its evolutionary possibilities optimally, when its genome length lies closely below its critical length in relation to the error threshold of the replication (as mentioned above).

Now, the correlation between error threshold and viral replication and the genome length is neglected according to the invention. That means, that the error threshold must be exceeded with the replication, such that the genetic information of the respective infective virus flows off. This happens the better, the stronger the respective virus individual is reproduced. This conception is running counter to all known intentions and conceptions to dam up viral infections by medicaments. Particularly when treating HIV, efforts are rather made to suppress the mechanism, by which the virus evidently succeeds to escape to all attempts of the immune system to suppress the virus reproduction and propagation by neutralizing antibodies and cellular defense mechanisms. In this way, it is known in the literature that HIV-variants in the immune dominant region V3 of the gp120 enable again and again a way out of neutralizing antibodies. Therefore, many therapeutic efforts are directed to inhibit the formation of variants, i.e., the formation of mutants, which just are formed and reproduced by defective replication. Apparently, the strategy according to the invention is, therefore, going into the wrong direction when being calculated to reproduce viruses more strongly. However, this is not the case since the virus does drastically lose infectedness as soon as it is reproduced beyond the error threshold with the replication systems and, particularly, when it is reproduced more vehemently.

It is known that the production of virus-resistant hostorganisms succeeds by interfering with an important regulating system of the virus replication. Viral information carriers will be reproduced only until a certain numerical upper limit in a host cell. Therefore, the replication is subject to a virus-coded control. Viral coat-proteins are often participating in this replication limit. When the first, respective translation products are occurring in a cell, they have certain loci at he replication source or at the control region of the replicase or polymerase and lead subsequently to a blocking of the replication initiation.

Basis of a series of endeavors for the treatment prophylaxis of viral diseases is the constitutive expression of the coat-proteins of pathogenic viruses via transgenic constructs. This endeavor is particularly followed in plant protection as transgenic plants express this viral coat-proteins. The constitutive expression of coat-proteins seems to cause a resistance towards a natural infection in several viruses. However, the fact that, for instance, the resistance is neutralized in a tobacco mosaic virus (TMV) when infecting with naked RNA, is indicating that very different resistance mechanisms could explain the effect of the coat-proteins.

The virus-coded blocking of the replication at a certain numerical upper limit has a significant importance from the point of view of the virus. When in a host cell replication copies of a virus represent self-again the matrix for a replication in the same host cell, this means, that already defectively replicated genomes form the matrix of further replication rounds, such that in the next replication round further defective copies are formed. Viruses which, correspondingly, replicate according to the so called "rolling-circle-principle", have found a way out of the dilemma by only functioning one copy, respectively, as a matrix.

When strongly defective genomes are synthesized by using replication products as matrix within a cell, this will be initially without consequences since no selection of the forming viruses in relation to infectivity is occurring. Non-functional genes or also genes which will lead to products of inferior value, as for instance to a replicase with a high rate of error, can be complemented in trans. In this way, viral genomes are finally "packed up", which are replicated by replicases with high rate of misincorporation beyond the error threshold. Thereby, the "healthy" population (the quasi-species-distribution of the wild-type) of the viruses are diluted by insufficient viruses which are in a limited way infectious and replicationable in a limited way. This is not in accordance with a stable virus population as being favorable to the virus.

This mechanism will be explained more detailed in the example of the Qβ-infection in *E. coli.* About 1,000 replicase sub-units per cell are synthesized after the infection of the bacterial host, whereafter the translation of the replicase-locus is interrupted. The viral coat-protein could be identified for the translation principle having a binding site in the replicase-translation region.

An *E. coli* cell has only a limited capacity to synthesize phages, such that an excess production of viral genomes is superfluous. A. Schwienhorst and B. Lindemann have confirmed by experiment that fatal consequences will appear to the virus when too many defective genome copies and, consequently, defective replicase copies are formed. Upon replication of the +Qβ-RNA within a cell, not only the original matrix is used, but also the replication products thereof, which represent statistically in its majority, according to the conception of the quasi-species-distribution, 1 to 2 error mutants. Since these mutants within a host are not subject to many selection criteria, e.g. their infectivity, many unfavorable virus variants are accumulated. Therefore, the virus population consisting of quasi-species-distributions which are produced with about 1,000 replication molecules per cell can survive in a stable form.

However, when the coat-protein transmitted regulation mechanism is canceled, as well the above described effect as the problem of the protection with transgenic coat-protein-producers as target cells will immediately become clear. *E. coli* cells which are transformed in such a way, were infected with Qβ-phage. In the beginning, an effective protection of the host cells by blocking of the replicase-translation could be observed as expected. However, after some time resistant variants were observed which had been induced by the selection pressure. A more detailed analysis revealed that under these conditions of selection such virus-RNA-mutants succeed which binding site for the coat-protein were defective and, therefore, could no more be repressed by coat-protein. It is assumed that also the limitation of the replicase synthesis being canceled in this way.

Due to this fact, it is pointed out that this relatively modern trial, namely to use transgenically expressing coat-proteins, will also produce permanently resistant virus mutants. To come to this, no long period is needed when, as in the case of the replication blocking with Qβ-phage, only a single point mutation breaks through the resistance barrier.

On the other hand, the strategy according to the invention, which in the meaning of an information conservation is producing mutants which are too strongly subject to errors, leads via a period of longer lasting infection to a degeneration of the quasi-species-distribution, corresponding to the wild-type virus and, therefore, to the extinction thereof. This will occur according to the invention when the rate of misincorporation of the defective replication system is situated only unessentially above the evolutionary optimized error threshold. The error rate of the virus replication will be elevated according to the invention above the evolutionary admissible threshold, whereby the replication must not be inhibited but at least should proceed as efficient as the one of the wild-type virus. This can be accomplished by various measures.

In this way, an active agent which interferes with a replication process in a way that it comes to a specific elevation of the rate of misincorporation of the viral replication system, can be used. By using the prior antiviral screening systems such an active agent cannot be identified.

The use of a system such as it is described according to the invention, in combination with in vitro-cell cultures, however, permits an effective screening to such mutants of a polymerase from samples of defective genome populations, as described above for *E. coli*-viruses.

The screening to HIV is carried out, e.g., with cloned HIV-variants in infected target cells like peripheral blood cells or transformed lymphocyte cells like HUT 78. Thereby, the virus replicating system is incubated with potential active agents of different concentrations. A representative gene locus of the virus-RNA or virus-DNA is then, after the cultivation being effected, in vitro amplified with a polymerase having a low error rate. The amplification product will be hybridized with a responsive, cloned probe of the starting variants and, e.g., examined by a detection system as described in PCT/EP 90/01366 for the presence of incorrect virus variants which are amplified within the cells. In this way, such active agents can be detected that exceed the error threshold, which, however, do not prevent a replication and not necessarily influence measurably the infectivity. From such active agents can be expected that they also can act allosterically. Therefore, they should also not interact inevitably with cellular polymerase systems, contrary to conceptions which are based on the principle of antimetabolites, e.g. nucleotide analogue as AZT. When the replication per se is not stopped immediately, also in addition to this, no direct feedback is to be expected which helps a therapy resistant point mutant to get immediately a vital selection advantage.

The process according to the invention can be a used in a particularly preferred embodiment when transgenic systems are used, as it is already practiced in the plant sector with the coat-protein production. Stem cells without differentiated potential receiver cells of infected or endangered patients can be transformed with a gene for a virus polymerase (RNA-replicase, reverse transcriptase or DNA-dependent DNA-polymerase) with elevated error rate, which can be obtained by the above mentioned screening process. Whatever virus mutants produces a defective replication, they will encounter a target cell which already provides the viral replication system with elevated rate of misincorporation or decisive co-factors or subunits thereof. All of the virus variants are replicated above their characteristic error threshold. In this way, no virus variant is able to develop resistances. The information will flow off with further amplification. The process will be the more efficient the less the virus amplification is inhibited per se.

The conception of the protection of host cells against viral infections by surpassing the error threshold of the virus-specific replicase/polymerase through maintenance of the replication efficiency can be described more in detail in the example of *E. coli* for the Qβ virus, if *E. coli* is transformed with the replication gene under control of his own promoter. In this case, the replicase stems from the mutant spectrum of Qβ and must have an elevated rate of misincorporation in relation to the viral wild-type. However, the replication efficiency of the replicase must not be different in cell-free in vitro-systems, e.g. by the replication of midi variants and mini variants, from that of the wild-type replicase. The *E. coli* cells containing replicase mutant, as model systems of gene treated potential host cells, can be, e.g., infected transiently in the "cell stat" with wild-typeQβ-phages. After an initial infection, the. number of plaques per ml diminishes evidently in relation to not transformed cells. However, the infection with T-phage is proceeding for both cell types in a similar way, as was to be expected, since the Qβ-replicase does not interfere during the replication of T-phage.

When host variants having lost resistance against Qβ-phage infection are appearing, it is no effect which is contrary to the present invention. In this case, the analyzed stems with recovered susceptibility are related to stem variants with defective mutant replicase or with a promoter variant, which are formed by defective E. coli replicase. This form of resistance built-up is also theoretically possible with higher cells, even if it is by reason of lower cell numbers and lower partition rates and higher precision of the replication more unlikely by order of magnitudes, such that it will be unimportant in the practice.

Several processes of different complexity are available in order to find out a suitable polymerase from a natural or artificial spectrum of mutants of a polymerase. A preferred source was already mentioned for *E. coli* bacteria, in order to fish replicases with elevated rate of misincorporation out of the spectrum of an enlarged quasi-species-distribution.

It has to be tested, if a different morphology of the above described Qβ-plaques can be attributed to a defective replicating polymerase (replicase). A simple genetic test is a plaque purification of the morphologically changed plaques. When the morphological peculiarity is maintained more or less uniformly, this fact will not indicate a mutation in the polymerase-gene section but in another segment of the poly-cistronic genome. However, when again plaques of a greater morphological diversity are formed, it will be a strong indication to a defectively working polymerase. The magnitude of the plaques in turn, can be rated as an indication of rapid synthesis kinetics. It was to expect that greater plaques also have a more rapid replicase. Thereby, the expenditure in relation to the molecular-biologically characterized finding of the desired species can be reduced.

It is possible, to reliably analyze an uncertain plaque by the technique of the temperature gradient gel electrophoresis, if it actually contains phages having a replicase with greater rate of misincorporation.

The temperature gradient gel electrophoresis can detect mutations in a certain nucleic acid segment in a highly sensitive manner. In this way, also mutants can be found in a population of sequences. The proof of mutants is normally performed on the plane of a twin-threaded DNA. In this way, a mutant spectrum can also be analyzed of in vitro amplified nucleic acid segments by transforming almost all mutants into heteroduplexes in a denaturation/renaturation step, after the amplification being realized (see FIG. 5). When a specific sequence, as for instance a cloned segment, is present in an excessive amount, an under-represented mutant will no more find after the denaturation its own counter strand. On the contrary, it forms heteroduplexes with other counter strands, statistically the most frequently with the most frequently occurring sequence. Whereas the homoduplexes are migrating on a parallel temperature gradient electrophorese gel in a band of highest mobility, the different heteroduplexes will be retarded specifically along the temperature gradient since the molecules will be unfolded partially in single strand structures. Therefore, in a mixture of an excess of uniform structures with mutants of this sequence, the typical picture of FIG. 5, clone A-D, will be obtained. The homoduplexes are migrating in the most rapidly migrating band, followed by a crowd of bands of different heteroduplexes (PCT/EP 90/01366).

From the intensity of the mutant bands in relation to the intensity of the homoduplex band can be concluded to the relative frequency of the mutants, respectively, to the rate of misincorporation of the replicating enzyme system (W. Thilly). In an analogous manner, a population of specific sequences can be tested in the meaning according to the invention which are formed by help of the procured, defective polymerase. These fragments can be tested either directly in the temperature gradient electrophorese gel system, or after amplification as by PCR-reaction with or without previous transcription in DNA by a reverse-transcriptase.

A radio-labelled segment can preferably be added to the mixture, the frequency of which is identical to the one of the homoduplex in order to estimate the error rate of a replicase. In this way, the radioactivities of the homoduplex band and that of the heteroduplexes can be determined by counting after the denaturation and renaturation being realized (FIG. 5). The ratio of the measured activities is then a direct measure for the error rate of the replicating system, respectively, of the replicase. It is a prerequisite during the introduction of an enzymatic amplification step that the error rate of the amplification step is small in relation to the error rate of the preceding replication.

Figure 6:
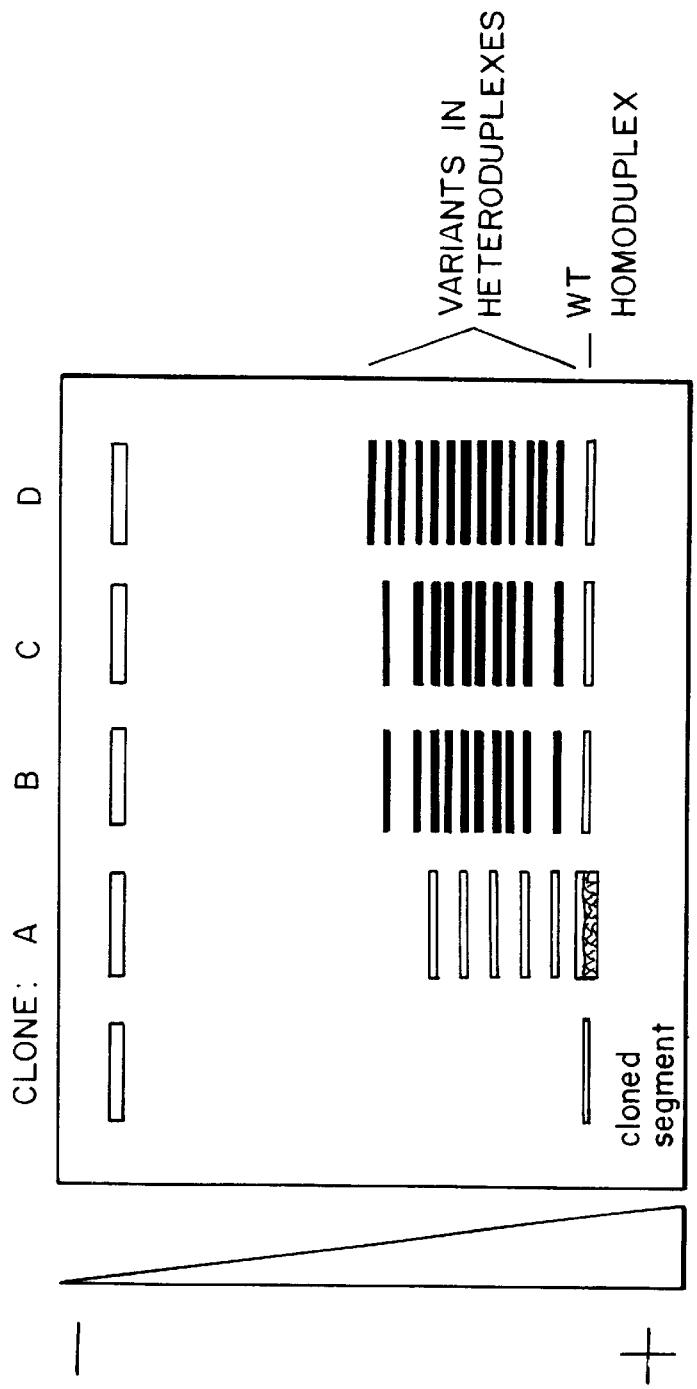

The enlargement—schematically described in FIG. 6—of the quasi-species-distribution with progressing infection time with replication under considerable participation of the defective polymerase can be observed by this process. Whereas the mutant distribution without changing selection stress remains approximately constant in the infection of a not transformed cell population having a wild-type virus, an enlargement of the quasi-species-distribution occurs when the defective replication process according to the invention is participating. This will be seen in the temperature gradient gel electrophorese analysis by an increasing rate of the band intensity of the mutant spectrum in relation to the band having the greatest relative frequency, previously called wild-type.

The temperature gradient gel electrophorese system can also be used to measure the efficiency, i.e. the replication velocity in the above described meaning, respectively, to compare it with the one of the wt-enzyme. As described by Henco et al. [Nucleic Acids Res. (1990)], the temperature gradient gel electrophorese system can be used for the exact quantification of nucleic acids in a probe, whereby the accuracy being ±15%. In this way, the relative synthesis power of a wild-type polymerase and of a mutant polymerase can be quantified in a cell-free in vitro system or cell culture by means of their respective nucleic acid synthesis products.

The described processes can be used analogously for the discovery and classification of polymerase mutants of other virus/host systems which are applicable according to the invention. When in bacteria, as in the case of tobacco mosaic virus (TMV)—in analogy to the plaque formation—clonal, virus caused lesions can be detected in leafs, exits the possibility to conclude from the morphology of single lesions to the presence of viral polymerase mutants with elevated rate of misincorporation. TMV causes necrotic local lesions to N-gene-tobacco (N. glutinosa, N. tabacum cv. Xanthi-nc, respectively, Samsun NN) [Atabekov]. The reactions lead to localization of the virus infection around the sites of the primary infestation. Temperature sensitive mutants are not able to form the respective product in a functional state at elevated temperatures (e.g., 32° C.). Such mutants are existing as well for the coat protein a for the transport protein. The functions of the RNA-covering, respectively, of the cell-to-cell transport are disturbed under non permissive conditions. On the other hand, the necrotic reaction of the N-gene-tobacco is also temperature dependent. The localization fails to appear and the TMV (wild-type) is spread over the leaf spreading at elevated temperature (e.g., 32° C.). A collapse of the tissue will occur when returning to normal temperature. The necrotization leads to large-area, pergament-like segments. By combined use of N-gene-tobacco and Ts-mutants another picture can be expected. Even if the necrotization and localization fails to appear at elevated temperatures, no virus spreading will occur since the transport function is switched off under non permissive conditions. A necrosis formation will occur when returning to normal temperature, as if a temperature treatment never had been performed. Since it is a matter of well characterized point mutants in the case of the experimental mutants of the virus, the rate or back-mutation can be estimated by defective replicase activity by of the symptom picture after differential temperature treatment.

What is claimed is:

1. A method of destabilizing viral quasi-species comprising treating a target cell with a replicator nucleic acid.

2. The method according to claim 1, wherein the replicator nucleic acid has a) a shorter intracellular replication time than a natural viral substrate nucleic acid;

b) a binding constant to a vital polymerase greater than a natural viral substrate nucleic acid; and c) few or no binding sites for effectors exerting negative feedback-effect on replication.

3. The method according to claim 1, wherein the target cells are monocellular organisms or bacteria.

4. The method according to claim 1, wherein the target cells are blood cells or erythropoietic stem cells.

5. The method according to claim 1, wherein the target cells are plant cells or animal cells.

6. The method according to claim 1, wherein the replicator nucleic is obtained by a) reacting nucleotides in the presence of a viral replication system and other factors necessary for the reproduction of viruses to form oligo- or polynucleotides, and b) exclusively selecting oligo- or polynucleotides that are maximally amplified by said viral replication system and lacks one or more genes essential to the virus.

7. The method according to claim 1, wherein the nucleic acid is homologous to oligo- or polynucleotides produced by treating a target cell with a replicator nucleic acid produced from a replicator precursor by nucleolytic degradation.

8. The method according to claim 1, wherein the replicator nucleic acid is produced from a replicator precursor by nucleolytic degradation.

9. The method according to claim 8, wherein the nucleolytic degradation is performed by nucleolytic enzymes.

10. The method according to claim 9, wherein the enzyme is RNase P.

11. The method according to claim 8, wherein the replicator precursor contains a ribozymic structure.

12. The method according to claim 1, wherein the viral quasi-species is a RNA-virus species.

13. A method of treating viral infections comprising the steps of administering a replicator nucleic acid or a replicator precursor to a patient in need thereof.

14. The method according to claim 12, wherein the viral infection is an infection with an RNA virus.

* * * * *

UNITED STATES PATENT AND TRADEMARK OFFICE
CERTIFICATE OF CORRECTION

PATENT NO. : 6,423,516 B1
DATED : July 23, 2002
INVENTOR(S) : Eigen et al.

It is certified that error appears in the above-identified patent and that said Letters Patent is hereby corrected as shown below:

<u>Title page,</u>
Item [22], the PCT filing date correctly should read:
-- July 2, 1993 --

Signed and Sealed this

Third Day of May, 2003

JAMES E. ROGAN
*Director of the United States Patent and Trademark Office*